United States Patent [19]

Seidelmann et al.

[11] Patent Number: 4,894,377
[45] Date of Patent: Jan. 16, 1990

[54] β-CARBOLINES AND THEIR USE AS MEDICINAL AGENTS

[75] Inventors: Dieter Seidelmann; Ralph Schmiechen; Andreas Huth; Dieter Rahtz, all of Berlin, Fed. Rep. of Germany; Claus T. Braestrup, Roskilde; Mogens Engelstoft, Vaerlose, both of Denmark

[73] Assignee: Schering Aktiengesellschaft, Berlin and Bergkamen, Fed. Rep. of Germany

[21] Appl. No.: 3,179

[22] Filed: Jan. 14, 1987

Related U.S. Application Data

[63] Continuation of Ser. No. 623,610, Jun. 22, 1984, abandoned.

[30] Foreign Application Priority Data

Jun. 23, 1983 [DE] Fed. Rep. of Germany ....... 3322895

[51] Int. Cl.$^4$ .................... C07D 471/14; A61K 31/40
[52] U.S. Cl. .................... 514/292; 514/255; 514/228.2; 514/232.8; 546/86; 544/60; 544/126; 544/361
[58] Field of Search .................... 546/86; 544/60, 126, 544/361; 514/292, 222, 236, 239, 255

[56] References Cited

U.S. PATENT DOCUMENTS 4,371,536 2/1983 Braestrup et al. .................... 546/86

FOREIGN PATENT DOCUMENTS 0054507 12/1981 European Pat. Off. .............. 546/86

Primary Examiner—Jane T. Fan
Attorney, Agent, or Firm—Millen, White & Zelano

[57] ABSTRACT

β-Carbolines of general Formula I

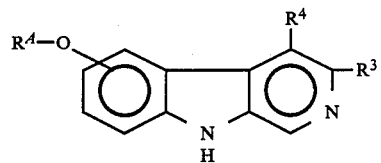

wherein $R^3$ is

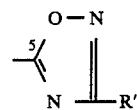

or —COOR″, wherein R′ is $C_{1-3}$ alkyl or $C_{3-6}$ cycloalkyl and R″ is $C_{1-4}$ alkyl; $R^4$ is hydrogen, methyl, ethyl or methoxymethyl; and $R^A$ is

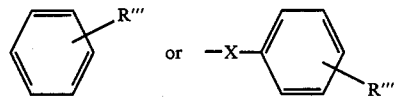

wherein X is $C_{1-12}$ straight-chain, branched-chain, saturated or unsaturated alkyl or a corresponding alkyl group with a $CH_2$-group substituted by a carbonyl group and R″″ is one or more of fluorine, chlorine, bromine, or iodine, $C_{1-3}$ alkyl, $C_{1-3}$ alkoxy, $C_{1-5}$ acyloxy, phenyl, $C_{2-5}$ alkylenedioxy, trifluoromethyl, nitrilo, nitro or —$NR^{IV}R^V$ wherein $R^{IV}$ and $R^V$, which can be the same or different are hydrogen, $C_{1-3}$ alkyl, $C_{1-5}$ acyl or phenyl, or collectively with the amido nitrogen atom form a 3- to 6-membered hetero ring, which are prepared conventionally by esterifying a corresponding compound wherein $R^4$ is H or $R^3$ is —COOH, exhibit effects on the central nervous system and can be used as psychorharmaceuticals.

25 Claims, No Drawings

β-CARBOLINES AND THEIR USE AS MEDICINAL AGENTS

This is a continuation of application Ser. No. 623,610 filed June 22, 1984, now abandoned.

BACKGROUND OF THE INVENTION

This invention relates to novel substituted β-carbolines and pharmaceutical compositions comprising them, to a process for the preparation thereof, and to the use thereof as medicinal agents.

SUMMARY OF THE INVENTION

In a composition aspect, this invention relates to β-carbolines of general Formula I:

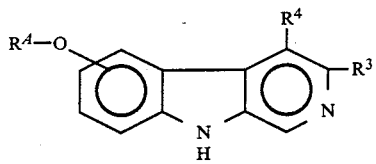
(I)

wherein $R^3$ is a 5-oxadiazolyl group of the formula:

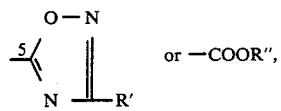 or —COOR″, wherein R′ is $C_{1-3}$ alkyl or $C_{3-6}$ cycloalkyl and R″ is $C_{1-4}$ alkyl; $R^4$ is hydrogen, methyl, ethyl or methoxymethyl; and $R^A$ is aryl of the formula

or aralkyl of the formula

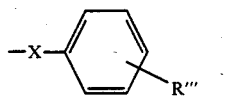

wherein X is $C_{1-12}$ straight-chain, branched-chain, saturated or unsaturated alkyl or a corresponding alkyl group with a $CH_2$-group substituted by a carbonyl group, and R‴ is one or more of fluorine, chlorine, bromine, or iodine, $C_{1-3}$ alkyl, $C_{1-3}$ alkoxy, $C_{1-5}$ acyloxy, phenyl, $C_{2-5}$ alkylenedioxy, trifluoromethyl, nitrilo, nitro or —$NR^{IV}R^V$ wherein $R^{IV}$ and $R^V$, which can be the same or different, are hydrogen, $C_{1-3}$ alkyl, $C_{1-5}$ acyl or phenyl, or collectively with the amido nitrogen atom form a 3— to 6-membered hetero ring.

In a process aspect this invention relates to a process for the production of β-carbolines of general Formula I wherein (a) a substituted hydroxy-β-carboline of general Formula II

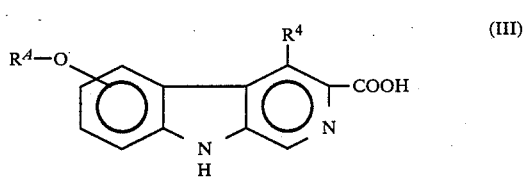
(II)

wherein $R^3$ and $R^4$ have the values given above is reacted in a conventional manner with an esterification reagent of the general formula $R^A Y$, wherein Y is chlorine, bromine, iodine or tosyl, and $R^A$ has the values given above, and, if desired, the thus-obtained compound of Formula I wherein R″ stands for methyl or ethyl is conventionally transesterified; or (b) a substituted β-carboline-3-carboxylic acid of general Formula III

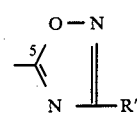
(III)

wherein $R^A$ and $R^4$ have the values given above, is reacted in conventional manner with an amidoxime of the general formula R′—C(=NOH)NH$_2$ wherein R′ has the values given above, to the corresponding 5-oxadiazolyl derivative.

In a further composition aspect, this invention relates to pharmaceutical compositions comprising a compound of general Formula I in admixture with a pharmaceutically acceptable carrier.

In a method-of-use aspect, this invention relates to the use of compounds of general Formula I as psycho-pharmaceuticals.

DETAILED DISCUSSION

Examples of groups of compounds of general Formula I are those wherein
 (a) $R^3$ is a 5-oxadiazolyl group of the formula

wherein R′ is $C_{1-3}$ *alkyl*;
 (b) $R^3$ is —COOR″ wherein R″ is —$CH_3$ or $C_2H_5$;
 (c) $R^A$ is —*alkylene*

wherein alkylene is —$CH_2$— or —$CH(CH_3)$— and $R^{III}$ is one or two of *fluoro, chloro, bromo,* —$CH_3$, —$OCH_3$, —$NO_2$ or —$CF_3$, especially those wherein —$OR^A$ is in the 5-position and is$R^{III}$ *monofluoro*;
 (d) $R^4$ is H, e.g., those of groups (a), (b) and (c);
 (e) $R^4$ is $CH_3$, e.g., those of groups (a), (b) and (c);
 (f) $R^4$ is $C_2H_5$, e.g., those of groups (a), (b) and (c); and (g) $R^4$ is $CH_3OCH_2$, e.g., those of groups (a), (b) and (c).

The novel β-carbolines of general Formula I are substituted in the 3-position by a 3-substituted-5-oxadiazolyl group or by an alkoxycarbonyl group. Examples of 3-substituents on the 5-oxadiazolyl group are methyl, ethyl, n-propyl-isopropyl, cyclopropyl, cyclopentyl, cyclohexyl, carbomethoxy, carbethoxy, carbopropoxy and carbobutoxy.

In Formulae I through III, alkyl can be straight- or branched-chain, e.g., methyl, ethyl, propyl, isopropyl, n-butyl, isobutyl and tert-butyl.

The 4-position substituent of the novel β-carbolines is hydrogen, lower alkyl, e.g., methyl or ethyl, or methoxymethyl. The $R^4$—O— is preferably in the 5— or 6—position of the β-carbolines. The bridging X group is preferably methylene or alkyl-substituted methylene, e.g., —CH(CH₃)— or —CH(C₂H₅)—. The R‴ substituent on the $R^4$ aryl or aralkyl group represents from 1 to 4, preferably 1 or 2, substituents on the phenyl ring, which can be alike or different. Preferably at least one such substituent is halogen. Examples of such substituents are acetoxy, propionyloxy, t-butyryloxy, 2,3-methylenedioxy, 3,4-ethylenedioxy, amino, methylamino, diethylamino, acetamido, benzamido, ethyleneimino, 2′-methyl pyrrolidino, piperidino, morpholino, thiomorpholino, N-methylpiperazino. The cycloalkyl groups can bear one or more simple substituents, preferably alkyl and most preferably methyl or ethyl, on the ring carbon atoms. The heterocyclic amino substituents can contain from 0–2 ring heteroatoms, e.g., N, S and/or O, in addition to the ring nitrogen atom.

The compounds of this invention exhibit valuable pharmacological activities, including anticonvulsant, muscle relaxant, tranquilizing and anxiolytic activities. They influence, in particular, the central nervous system and are thus suitable for use as psychopharmaceuticals, e.g., as anticonvulsants for the treatment of epileptics.

It is known that certain sites in the central nervous system of vertebrates show a high specific affinity for binding 1,4— and 1,5-benzodiazepines (Squires, R. F. and Braestrup, C., Nature (London) 266 (1977) 734). The sites are called benzodiazepine receptors. It has been found that the substituted β-carbolines of general Formula I, although greatly different in their chemical structure from benzodiazepines, surprisingly exhibit a strong affinity and specificity for binding to these benzodiazepine receptors in that they displace radioactively tagged flunitrazepam from these benzodiazepine receptors.

The displacement activity of the compounds of the invention is indicated in the Table shown below as the $IC_{50}$ and $ED_{50}$ values. The $IC_{50}$ value indicates the concentration effecting a 50% displacement of the specific binding of $^3H$ flunitrazepam (1.0 nM, 0° C.) in specimens with a total volume of 0.55 ml of a cerebral membrane suspension, for example from rats.

The displacement activity is determined by in vitro test as follows:

0.5 ml of a suspension of untreated rat cerebrum in 25 mM $KH_2PO_4$, pH=7.1 (5–10 mg of tissue/specimen) is incubated for 40–60 minutes at 0° C. together with $^3H$ diazepam (specific activity 14.4 Ci/mmol, 1.9 nM) or $3_H$ flunitrazepam (specific activity 87 Ci/mmol, 1.0 nM). After incubation, the suspension is filtered through a porous glass plate, the residue is washed twice with cold buffer solution, and the radioactivity is measured by means of a scintillation counter.

Then the test is repeated, but in such a way that prior to adding the radioactively tagged benzodiazepine, there is introduced a certain quantity or an excess amount of the compound, the displacement activity of which is to be determined. The $IC_{50}$ value is calculated on the basis of the thus-obtained data.

The $ED_{50}$ value represents the dose of a test compound effecting a reduction of the specific binding of flunitrazepam to the benzodiazepine receptor in a living brain to 50% of the control value.

The in vivo test is performed as follows:

Groups of mice are injected with the test compound at varying doses and normally subcutaneously. After 15 minutes, the mice receive the $^3H$ flunitrazepam intravenously. After another 20 minutes, the mice are sacrificed, their forebrain membranes are removed, and the radioactivity of the forebrain membranes is measured by scintillation counter. The $ED_{50}$ value is determined with the aid of the dose/effect curves.

The compounds of this invention show, in a pharmacological test, anxiolytic, antiaggressive, and anticonvulsive activities. Two testing systems were employed to examine the anticonvulsive effect. The elimination of convulsions induced, on the one hand, by pentylenetetrazole (Pentazol) and, on the other hand, by 6,7-dimethoxy-4-ethyl-β-carboline-3-carboxylic acid methyl ester (DMCM) was examined. Pentazol and DMCM, respectively, are administered 15–30 minutes after intraperitoneal administration of the test compound in an amount of 15 mg/kg as an aqueous solution (pH 7) intraperitoneally and, respectively, in an amount of 150 mg/kg as a hydrochloric acid solution (pH 2–3) subcutaneously. These quantities induce clonic and tonic convulsions leading to death in untreated animals. The number of mice exhibiting convulsions and the number of mice which died 30 minutes after administration of Pentazol and DMCM, respectively, are recorded.

TABLE

| Substituent R‴ | $IC_{50}$ ng/ml (in vitro) | $ED_{50}$ mg/ml (in vivo) | $ED_{50}$ Pentazol | mg/kg DMCM | lll dB |
|---|---|---|---|---|---|
| 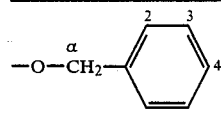 | 2 | 4 | 15 | 0.6 | 0.5 |
| 2-fluoro | 0.3 | 1.1 | 13 | 0.4 | 0.05 |
| 3-fluoro | 0.3 | 2.1 | 12 | 0.3 | 0.05 |
| 4-fluoro | 0.4 | 0.5 | 30 | 0.1 | 0.2 |
| 3-chloro | 1.4 | 2.8 | 0.9 | 0.3 | 0.08 |
| 4-chloro | 0.9 | 5.6 | >30 | | |
| 3,4-dichloro | 2.1 | 16 | 6 | 2.2 | |

TABLE-continued

| Substituent R''' | $IC_{50}$ ng/ml (in vitro) | $ED_{50}$ mg/ml (in vivo) | $ED_{50}$ Pentazol | mg/kg DMCM |111 dB |
|---|---|---|---|---|---|
| 3-bromo | 0.8 | >9 | 6 | | |
| 3-methoxy | 0.5 | 3.7 | >100 | | |
| 4-methyl | 0.9 | 10 | 30 | | |
| 3,4-dimethyl | 1.7 | 14 | 30 | | |
| 3-trifluoromethyl | 1.4 | 12 | 12 | | |
| 4-nitro | 0.2 | 11 | >50 | | |
| α-methyl | 1.1 | 0.5 | 3 | 0.1 | 0.01 |
| α-methyl, 3-chloro | 4.3 | 1.3 | 2 | | |
| —OC$_2$H$_4$—C$_6$H$_5$ | 0.8 | 6.4 | 40 | | |
| —OC$_3$H$_6$—C$_6$H$_5$ | 1.9 | 16 | 30 | 5.5 | |

Pharmacological Properties of R'''-Substituted 5-Benzyloxy-4-methoxymethyl-β-carboline-3-carboxylic Acid Ethyl Esters
DMCM = 6,7-Dimethoxy-4-ethyl-β-carboline-3-carboxylic acid methyl ester The $ED_{50}$ values indicated in the table were determined according to the method by Litchfield and Wilcoxon (1949) as the amount of antagonistically active compound required to protect 50% of the animals from convulsions and death.

The compounds of this invention also show a convulsion-relieving and/or convulsion-eliminating effect in the audiogenic seizure test. For this purpose, 18-21 day old male mice weighing 8-12 g (DBA/2 mice) receive intraperitoneally the compound to be tested as an ultrasound microsuspension in water/"Cremofor" EL (95:5) 30 minutes prior to testing. The animals are then exposed, in a soundproof wooden box (25×22×15 cm), to a sinusoidal sound of 14 kHz at 111 dB. The sound is generated immediately after transferring the animal into the box. Occurrence of clonic convulsions is recorded for 30 seconds. The $ED_{50}$ value in the table indicates the dose at which 40% of the mice show no convulsions at 111 dB (80% of the control mice show convulsions at 111 dB).

In addition to their other pharmacological uses, based on their biological efficacy in the foregoing tests, the compounds of this invention can be used as psychopharmaceuticals in human medicine. In this connection, they can be utilized formulated into pharmaceutical preparations, for example for oral and parenteral administration.

Formulating aids suitable herein are physiologically compatible, organic and inorganic excipients inert with respect to the compounds of this invention.

Examples of such excipients are water, salt solutions, alcohols, polyethylene glycols, polyhydroxyethoxylated castor oil, gelatin, lactose, amylose, magnesium stearate, talc, silicic acid, fatty acid mono- and diglycerides, pentaerythritol fatty acid esters, hydroxymethylcellulose, and polyvinylpyrrolidone.

The pharmaceutical preparations can be sterilized and/or combined with auxiliary agents, such as lubricants, preservatives, stabilizers, wetting agents, emulsifiers, buffers, and colorants.

Especially suitable for parenteral administration are injection solutions or suspensions, particularly aqueous solutions of the active compounds in polyhydroxyethoxylated castor oil.

For oral administration, particularly suited are tablets, dragees, or capsules with talc and/or a hydrocarbon excipient or binder, e.g., lactose, cornstarch or potato starch. Use can also be in liquid form, for example as an elixir to which a sweetener is added, if desired.

The compounds of this invention are admixed in dosage units of 0.05-10 mg of active material, with a physiologically acceptable carrier or vehicle.

The compounds of this invention are generally administered at a dosage rate of 0.1-300 mg/day, preferably 1-30 mg/day.

The compounds of this invention according to general Formula I are prepared by conventional methods.

Etherification of the β-carboline derivative of Formula II hydroxylated in the A ring takes place by reaction with a reactive aryl or aralkyl compound in a polar solvent, e.g., ethanol, acetonitrile, or dimethylformamide, in the presence of an alkali metal carbonate such as, for example, potassium carbonate or a base such as, for example, potassium hydroxide, 1,5-diazabicyclo[5.4.-0]undec-5-ene (DBU) and 1,4-diazabicyclo[2.2.2]octane (Dabco). (DBU) and 1,4-diazabicyclo[2.2.2]octane (Dabco). Especially suitable as the reactive aryl or aralkyl compound are the halogenides, such as the chloride, bromide, and iodide, as well as mesylates and tosylates.

For esterification, the free β-carboline-3-carboxylic acid is converted, for example with cesium carbonate, into the cesium salt and then made to react with the corresponding alkyl halogenide.

For transesterification, the present ester of Formula I is heated with an alcohol R''OH in the presence of catalytic amounts of R''ONa or NaH for 3-6 hours to temperatures of between 60° and 20° C. Optionally, transesterification can also take place with the alcohol R''OH in the presence of an acidic catalyst, such as p-toluene-sulfonic acid, hydrochloric acid, or copper-(II) chloride.

When $R^3$ represents a 5-oxadiazolyl group, the free β-carboline-3-carboxylic acid of Formula III is made to condense, at the reflux temperature of the reaction mixture, with an amidoxime of the formula R'-

C(=NOH)NH₂ in a solvent boiling above 100° C. and inert with respect to the reactants. Suitable solvents for the condensation reaction are, for example, toluene and dimethylformamide.

Suitably, the free β-carboline-3-carboxylic acid of Formula III is activated in a suitable way before the condensation reaction. It is possible to convert the acid to the mixed anhydride, to the activated ester, or to the chloride. Activation with imidazole/thionyl chloride in an aprotic solvent such as dioxane, tetrahydrofuran, dimethylformamide, or N-methylpyrrolidone at temperatures of between 0° and 50° C., preferably at room temperature, have proved satisfactory.

The starting β-carbolines of Formulae II and III also can be produced by conventional methods, e.g., U.S. Pat. Nos. 4,371,536 and 4,435,403.

Contemplated equivalents of the compounds of this invention are those otherwise corresponding to general Formula I which have comparable pharmacological activities and wherein R', R''' and/or R⁴ is a different substituent.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Preparation of Starting Material

The starting materials can be prepared by various methods, e.g., as described below.

Method (a)

10 g of 5-benzyloxy-4-methoxymethyl-β-carboline-3-carboxylic acid ethyl ester is refluxed for 3 hours in 100 ml of ethanol with 4 g of Raney nickel. After the catalyst has been removed by filtration, the filtrate is concentrated under vacuum. The residue is chromatographed over silica gel with methylene chloride+ethanol/1000+75, thus obtaining 7.2 g of 5-hydroxy-4-methoxymethyl-β-carboline-3-carboxylic acid ethyl ester, mp 179°–181° C.

Method (b)

21 g of 5-benzyloxy-4-methoxymethyl-μ-carboline-3-carboxylic acid ethyl ester is hydrogenated in 250 ml of ethanol with 10 g of palladium/carbon (10%) for 3.5 hours at room temperature under normal hydrogen pressure. After filtration and concentration, the residue is chromatographed as in method (a), thus obtaining 15.1 g of 5-hydroxy-4-methoxymethyl-β-carboline-3-carboxylic acid ethyl ester, mp 179°–181° C.

Method (c)

2.19 g of 5-benzyloxy-4-methoxymethyl-3-ethoxycarbonyl-1,2,3,4-tetrahydro-β-carboline-1-carboxylic acid is heated under reflux for 3 hours with 0.2 g of palladium/carbon (10%) in 100 ml of xylene. After the catalyst has been filtered off, the filtrate is concentrated. The residue is chromatographed over silica gel (methylene chloride+ethanol/10+1), thus producing 0.57 g of 5-hydroxy-4-methoxymethyl-β-carboline-3-carboxylic acid ethyl ester, mp 179°–181°C.

The starting material utilized for this method can be prepared as follows:

37.6 g of 3-(4-benzyloxyindol-3-yl)-2-amino-5-oxahexanoic acid ethyl ester is dissolved in 200 ml of ethyl acetate. Under vigorous agitation, a solution of 10.8 g of glyoxylic acid monohydrate in 120 ml of water is added dropwise thereto. The reaction mixture is subsequently adjusted to pH 4 with 10% potassium carbonate solution and stirred for 14 hours at room temperature. The thus-precipitated yellow crystallized product is vacuum-filtered, washed with ethyl acetate, and dried, thus obtaining 20.3 g of 5-benzyloxy-4-methoxymethyl-3-ethoxy-carbonyl-1,2,3,4-tetrahydro-β-carboline-1-carboxylic acid as light-yellow crystals, mp 139°–142°C.

The following starting materials are prepared according to the methods (a), (b), and (c), indicated in parentheses:

6-hydroxy-4-methyl-β-carboline-3-carboxylic acid ethyl ester, mp 269°–270° C. (b+c);

6-hydroxy-4-ethyl-β-carboline-3-carboxylic acid ethyl ester, mp 260°–263° C. (b);

6-hydroxy-β-carboline-3-carboxylic acid ethyl ester, mp 248°–250° C. (decomposition), (b);

6-hydroxy-4-methoxymethyl-β-carboline-3-carboxylic acid ethyl ester, mp 164°–166° C. (b+c);

5-hydroxy-β-carboline-3-carboxylic acid ethyl ester, mp 255° C. (decomposition), (b);

5-hydroxy-4-methyl-β-carboline-3-carboxylic acid ethyl ester, mp 240°–243° C. (decomposition), (a+c);

5-hydroxy-4-ethyl-β-carboline-3-carboxylic acid ethyl ester, mp 188–190° C. (a).

The following examples illustrate the process and products of this invention.

EXAMPLE 1

Under a nitrogen atmosphere, 0.3 g of 5-hydroxy-4-methoxymethyl-β-carboline-3-carboxylic acid ethyl ester is refluxed for 4 hours in 60 ml of ethanol with 0.3 g of potassium carbonate and 0.174 g of 3-fluorobenzyl chloride. After filtration and concentration under vacuum, the residue is chromatographed over silica gel (methylene chloride +ethanol/1000+25), thus obtaining 0.167 g of 5-(3-fluorobenzyloxy)-4-methoxymethyl-β-carboline-3-carboxylic acid ethyl ester, mp 188.0° C.

EXAMPLE 2

Analogously to Example 1, the following compounds are produced from the 5-hydroxy-4-methoxymethyl-β-carboline-3-carboxylic acid ethyl ester and the corresponding substitute benzyl halogenide:

5-(2-fluorobenzyloxy)-4-methoxymethyl-β-carboline-3-carboxylic acid ethyl ester, mp 139°–140° C.;

5-(4-fluorobenzyloxy)-4-methoxymethyl-β-carboline-3-carboxylic acid ethyl ester, mp 174°–176° C.;

5-(4-chlorobenzyloxy)-4-methoxymethyl-β-carboline-3-carboxylic acid ethyl ester, mp 191°–193° C.;

5-(3-chlorobenzyloxy)-4-methoxymethyl-β-carboline-3-carboxylic acid ethyl ester, mp 196° C.;

5-(2-chlorobenzyloxy)-4-methoxymethyl-β-carboline-3-carboxylic acid ethyl ester, mp 174°–176° C.;

5-(2,5-dichlorobenzyloxy)-4-methoxymethyl-β-carboline-3-carboxylic acid ethyl ester, mp 191°–192° C.;

5-(3,5-dichlorobenzyloxy)-4-methoxymethyl-β-carboline-3-carboxylic acid ethyl ester, mp 165°–166° C.;

5-(2,6-dichlorobenzyloxy)-4-methoxymethyl-β-carboline-3-carboxylic acid ethyl ester, mp 209°–210° C.;

5-(3,4-dichlorobenzyloxy)-4-methoxymethyl-β-carboline-3-carboxylic acid ethyl ester, mp 172° C.;

5-(3-bromobenzyloxy)-4-methoxymethyl-β-carboline-3-carboxylic acid ethyl ester, mp 209° C.;

5-(3-trifluoromethylbenzyloxy)-4-methoxymethyl-β-carboline-3-carboxylic acid ethyl ester, mp 202° C.;

5-(4-nitrobenzyloxy)-4-methoxymethyl-β-carboline-3-carboxylic acid ethyl ester, mp 186° C.;

5-(3-methoxybenzyloxy)-4-methoxymethyl-β-carboline-3-carboxylic acid ethyl ester, mp 190° C.;

5-(2,4-dimethoxybenzyloxy)-4-methoxymethyl-β-carboline-3-carboxylic acid ethyl ester, mp 185° C.;

5-(3,4,5-trimethoxybenzyloxy)-4-methoxymethyl-β-carboline-3-carboxylic acid ethyl ester;

5-(2-nitro-3,4,5-trimethoxybenzyloxy)-4-methoxymethyl-β-carboline-3-carboxylic acid ethyl ester;

5-(3,4-ethylenedioxybenzyloxy)-4-methoxymethyl-β-carboline-3-carboxylic acid ethyl ester;

5-(3,4-methylenedioxybenzyloxy)-4-methoxymethyl-β-carboline-3-carboxylic acid ethyl ester, mp 212° C.;

5-(4-methylbenzyloxy)-4-methoxymethyl-β-carboline-3-carboxylic acid ethyl ester, mp 164° C.;

5-(3,4-dimethylbenzyloxy)-4-methoxymethyl-β-carboline-3-carboxylic acid ethyl ester, mp 188° C.;

5-(2-methyl-3-nitrobenzyloxy)-4-methoxymethyl-β-carboline-3-carboxylic acid ethyl ester;

5-[1-(3-chlorophenyl)ethoxy]-4-methoxymethyl-β-carboline-3-carboxylic acid ethyl ester, mp 166° C.;

5-[1-(4-chlorophenyl)ethoxy]-4-methoxymethyl-β-carboline-3-carboxylic acid ethyl ester, mp 158° C.;

5-(4-chlorophenacyloxy)-4-methoxymethyl-β-carboline-3-carboxylic acid ethyl ester, mp 204°–207° C.

EXAMPLE 3

Analogously to Example 1, the following compounds are produced from the 5-hydroxy-4-methyl-β-carboline-3-carboxylic acid ethyl ester and the corresponding substituted benzyl halogenide:

5-(2-chlorobenzyloxy)-4-methyl-β-carboline-3-carboxylic acid ethyl ester;

5-(3-methoxybenzyloxy)-4-methyl-β-carboline-3-carboxylic acid ethyl ester;

5-(2,4-dimethoxybenzyloxy)-4-methyl-β-carboline-3-carboxylic acid ethyl ester;

5-(3-trifluoromethylbenzyloxy)-4-methyl-β-carboline-3-carboxylic acid ethyl ester; and 5-(4-diethylaminobenzyloxy)-4-methyl-β-carboline-3-carboxylic acid ethyl ester.

EXAMPLE 4

The following compounds are prepared analogously to Example 1 from the 5-hydroxy-4-ethyl-β-carboline-3-carboxylic acid ethyl ester and the corresponding substituted benzyl halogenide:

5-(3-chlorobenzyloxy)-4-ethyl-β-carboline-3-carboxylic acid ethyl ester;

5-(3-fluorobenzyloxy)-4-ethyl-β-carboline-3-carboxylic acid ethyl ester; and

5-[1-(3-chlorophenyl)ethoxy]-4-ethyl-β-carboline-3-carboxylic acid ethyl ester.

EXAMPLE 5

Analogously to Example 1, the following compounds are prepared from the 5-hydroxy-β-carboline-3-carboxylic acid ethyl ester and the corresponding substituted benzyl halogenide:

5-(3-chlorobenzyloxy)-β-carboline-3-carboxylic acid ethyl ester;

5-(3-fluorobenzyloxy)-β-carboline-3-carboxylic acid ethyl ester;

5-(3,4,5-trimethoxybenzyloxy)-β-carboline-3-carboxylic acid ethyl ester; and 5-(3-dimethylaminobenzyloxy)-β-carboline-3-carboxylic acid ethyl ester.

EXAMPLE 6

The following compounds are prepared analogously to Example 1 from the 6-hydroxy-β-carboline-3-carboxylic acid ethyl ester and the corresponding substituted benzyl halogenide:

6-(3-chlorobenzyloxy)-β-carboline-3-carboxylic acid ethyl ester;

6-(4-fluorobenzyloxy)-β-carboline-3-carboxylic acid ethyl ester; and 6-(3,4-dimethylbenzyloxy)-β-carboline-3-carboxylic acid ethyl ester.

EXAMPLE 7

Analogously to Example 1, the following compounds are prepared from the 6-hydroxy-4-methoxymethyl-β-carboline-3-carboxylic acid ethyl ester and the corresponding substituted benzyl halogenide:

6-(3-chlorobenzyloxy)-4-methoxymethyl-β-carboline-3-carboxylic acid ethyl ester, mp 185°–187° C.;

6-(3,4-dichlorobenzyloxy)-4-methoxymethyl-β-carboline-3-carboxylic acid ethyl ester, mp 169°–170° C.;

6-(4-methylbenzyloxy)-4-methoxymethyl-β-carboline-3-carboxylic acid ethyl ester, mp 161° C.;

6-(4-nitrobenzyloxy)-4-methoxymethyl-β-carboline-3-carboxylic acid ethyl ester, mp 156° C. (decomposition); and 6-[1-(3-chlorophenyl)ethoxy]-4-methoxymethyl-β-carboline-3-carboxylic acid ethyl ester, mp 119° C.

EXAMPLE 8

Analogously to Example 1, the following compounds are produced from the 6-hydroxy-4-methyl-β-carboline-3-carboxylic acid ethyl ester and the corresponding substituted benzyl halogenide:

6-(3-chlorobenzyloxy)-4-methyl-β-carboline-3-carboxylic acid ethyl ester;

6-(3-fluorobenzyloxy)-4-methyl-β-carboline-3-carboxylic acid ethyl ester; and 6-(2,4-dimethoxybenzyloxy)-4-methyl-β-carboline-3-carboxylic acid ethyl ester.

EXAMPLE 9

Method A

One gram of the β-carboline-3-carboxylic acid ethyl ester substituted in the A ring is suspended and/or dissolved in 10 ml of the desired alcohol and, after adding 20 mg of copper(II) bromide, heated to 50° C. for 5–24 hours. The reaction time is determined by thin-layer chromatography. The reaction mixture is stirred into ice/water and the precipitated product is removed by filtration, washed with water, dried, and then recrystallized.

Method B

A solution is prepared from 10 ml of the desired and 100 mg of metallic sodium, then 1 g of the above-employed ethyl ester derivative is added, the reaction mixture is heated to 60°–80° C. and after completion of the reaction, worked up as in Method A.

The following compounds are produced by Method A:

5-(4-chlorobenzyloxy)-4-methoxymethyl-β-carboline-3-carboxylic acid n-propyl ester;

5-[1-(4-chlorophenyl)ethoxy]-4-methoxymethyl-β-carboline-3-carboxylic acid isopropyl ester; and 6-(3-fluorobenzyloxy)-4-ethyl-β-carboline-3-carboxylic acid n-butyl ester.

The following compounds are produced by Method B:

5-(2,4-dimethoxybenzyloxy)-4-methyl-β-carboline-3-carboxylic acid methyl ester;

5-(4-chlorophenacyloxy)-4-methoxymethyl-β-carboline-3-carboxylic acid n-propyl ester;

6-(4-chlorobenzyloxy)-4-ethyl-β-carboline-3-carboxylic acid methyl ester; and 6-(4-chlorobenzyloxy)-β-carboline-3-carboxylic acid ethyl ester.

EXAMPLE 10

0.2 g of 4-methoxybromobenzene, 0.3 g of 6-hydroxy-4-methoxymethyl-β-carboline-3-carboxylic acid ethyl ester, and 0.15 g of copper(I) oxide are heated in 5 ml of collidine to boiling for 35 hours. After cooling, the mixture is filtered and evaporated under vacuum. The residue is taken up in ethyl acetate, extracted repeatedly with ice-cold 25% ammonia solution and then washed with saturated sodium chloride solution, dried over calcium sulfate, and evaporated. Chromatography on silica gel with methylene chloride-ethanol (10:1) yields 0.17 g of 6-(4-methoxyphenoxy)-4-methoxymethyl-β-carboline-3-carboxylic acid ethyl ester, mp 154.0° C.

EXAMPLE 11

1.36 g of imidazole is combined in 15 ml of absolute tetrahydrofuran with 0.36 ml of thionyl chloride in 5 ml of absolute tetrahydrofuran. After 15 minutes of agitation at room temperature, the mixture is suctioned off from the precipitate. The filtrate is added to a suspension of 2.55 g of 5-(3-chlorobenzyloxy)-4-methoxymethyl-β-carboline-3-carboxylic acid in 50 ml of absolute dimethylformamide. After one hour of agitation at room temperature, the mixture is combined with 180 μl of water and then with 2.6 g of propionamidoxime, the tetrahydrofuran is removed by distillation, and the reaction solution is heated for 3 hours under reflux. After the solvent has been distilled off, the mixture is distributed in methylene chloride/saturated sodium bicarbonate solution, the organic phase is washed with saturated sodium chloride solution to render it neutral, dried over magnesium sulfate, and the solvent is distilled off under vacuum. The reaction product is recrystallized from 2-propanol, thus obtaining 1.3 g of 5-(3-chlorobenzyloxy)-3-(5'-(3'-ethyl-(1,2,4-oxadiazol))yl)-4-methoxymethyl-β-carboline, mp 182°–187° C.

5-(3-Chlorobenzyloxy)-4-methoxymethyl-β-carboline-3-carboxylic acid, utilized as the starting material, is obtained after saponification of the corresponding ethyl ester.

EXAMPLE 12

According to the method described in Example 11, the following compounds are prepared from the corresponding substituted β-carboline-3-carboxylic acid:

5-(1-phenyl ethoxy)-3-(5'-(3'-ethyl-(1,2,4-oxadiazol)-)yl)-4-methoxymethyl-β-carboline, mp 191°–198° C.;

5-[1-(3-chlorophenyl)ethoxy-]3-(5'-(3'-ethyl-(1,2,4-oxadiazol))yl)-4-methoxymethyl-β-carboline, mp 179°–181° C.;

6-(3-chlorobenzyloxy)-3-(5'-(3 -ethyl-(1,2,4-oxadiazol))yl)-4-methoxymethyl-β-carboline, mp 198°–202° C.; and 6-[1-(3-chlorophenyl)ethoxy]-3-(5'-(3'-ethyl-(1,2,4-oxadiazol))yl)-4-methoxymethyl-β-carboline, mp 153°–157° C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A substituted β-carboline of the formula

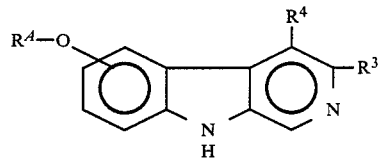

wherein $R^3$ is a 5- oxadiazolyl group of the formula

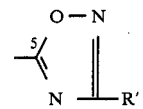

or —COOR″, wherein R′ is $C_{1-3}$ alkyl or $C_{3-6}$ cycloalkyl and

R″ is $C_{1-4}$ alkyl;

$R^4$ is hydrogen, methyl, ethyl or methoxymethyl; and $R^A$ is aryl of the formula

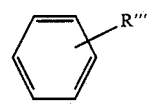

or aralkyl of the formula

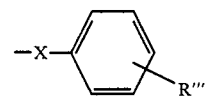

wherein X is $C_{1-12}$ is straight-chain, branched-chain, saturated or unsaturated alkyl or a corresponding alkyl group with a $CH_2$-group substituted by a carbonyl group and R‴ is one or more of fluorine, chlorine, bromine, or iodine, $C_{1-3}$ alkoxy, $C_{1-5}$ alkanoyloxy, benzoyloxy, phenyl, $C_{2-5}$ alkylenedioxy, trifluoromethyl, nitro or —$NR^{IV}R^V$ wherein $R^{IV}$ and $R^V$, which can be the same or different, are hydrogen, $C_{1-3}$ alkyl, $C_{1-5}$ alkanoyl, benzoyl or phenyl, or collectively with the nitrogen atom form an ethyleneimino, 2'-methyl pyrrolidino, piperidino, morpholino, thiomorpholino or N-methylpiperazino ring.

2. A compound of claim 1, wherein $R^3$ is —COOCH$_3$ or —COOC$_2$H$_5$.

3. A compound of claim 1, wherein —O—R$^4$ is in the 5— or 6-position.

4. A compound of claim 1, wherein X is —CH$_2$— or —CH(CH$_3$)—.

5. A compound of claim 1, wherein R$^4$ is methoxymethyl.

6. A compound of claim 1, wherein R$^4$ is —CH$_3$.

7. A compound of claim 1, wherein R$^4$ is —C$_2$H$_5$.

8. A compound of claim 1, wherein $R^3$ is —COOCH$_3$ or —COOC$_2$H$_5$, R$^4$ is CH$_3$OCH$_2$—, —O—R$^4$ is in the 5— or 6—position and R$^A$ is —alkylene

wherein alkylene is —CH$_2$— or —CH(CH$_3$)— and R''' is one or two of fluoro, chloro, bromo, —OCH$_3$, —NO$_2$ or —CF$_3$.

9. A compound of claim 8, wherein —O—R$^4$ is in the 5-position and R''' is monofluoro.

10. A compound of claim 6, wherein R'' is ethyl and R is —CH$_2$—.

11. 5—(3-Chlorobenzyloxy)—3—(5'-(3'-ethyl-(1,2,4-oxadizaol))yl-4methoxymethyl-β-carboline, a compound of claim 1.

12. 5-(3-Chlorobenzyloxy)-4-methoxymethyl-β-carboline-3-carboxylic acid ethyl ester, a compound of claim 1.

13. A compound of claim 1 wherein R' is cycloalkyl.

14. A compound of claim 1, wherein R''' is one or more of fluorine, chlorine, bromine, or iodine, C$_{1-3}$ alkoxy, C$_{1-5}$ alkanoyloxy, benzoyloxy, phenyl, C$_{2-5}$ alkylenedioxy, trifluoromethyl, nitro or —NR$^{IV}$R$^V$ wherein R$^{IV}$ and R$^V$, which can be the same or different, are hydrogen, C$_{1-3}$ alkyl, C$_{1-5}$ alkanoyl, benzoyl or phenyl, or collectively with the piperidino, morpholino, thiomorpholino or N-methylpiperazino ring.

15. A compound of claim 1, wherein R''' is one or more of C$_{1-3}$ alkoxy, C$_{1-5}$ alkanoyloxy, benzoyloxy, phenyl, C$_{2-5}$ alkylenedioxy, trifluoromethyl, nitro or —NR$^{IV}$R$^V$ wherein R$^{IV}$ and R$^V$, which can be the same or different, are hydrogen, C$_{1-3}$ alkyl, C$_{1-5}$ alkanoyl, benzoyl or phenyl, or collectively with the nitrogen atom form an ethyleneimino, 2'-methyl pyrrolidino, piperidino, morpholino, thiomorpholino or N-methylpiperazino ring.

16. A compound of claim 1, wherein R''' is one or more of C$_{1-3}$ alkoxy, C$_{1-5}$ alkanoyloxy, benzoyloxy, phenyl, C$_{2-5}$ alkylenedioxy, nitro or —NR$^{IV}$R$^V$ wherein R$^{IV}$ and R$^V$, which can be the same or different, are hydrogen, C$_{1-3}$ alkyl, C$_{1-5}$ alkanoyl, benzoyl or phenyl, or collectively with the nitrogen atom form an ethyleneimino, 2'-methyl pyrrolidino, piperidino, morpholino, thiomorpholino or N-methylpiperazino ring.

17. A compound of claim 1 wherein R''' is F.

18. A compound of claim 3 wherein R''' is 2-chloro.

19. A compound of claim 1 wherein R''' is 3-chloro.

20. A compound of claim 1 wherein R''' is 3-bromo.

21. A compound of claim 1 wherein R''' is halo.

22. A compound of claim 21, wherein O—R$^4$ is in the 5-position.

23. A pharmaceutical composition comprising an amount of a compound of claim 1 effective as an anticonvulsant in admixture with a pharmaceutically acceptable carrier.

24. A method of achieving an anticonvulsant effect in a patient comprising administering an effective amount of a compound of claim 1.

25. A method of claim 24 wherein the effect is an anti-epileptic one.

* * * * *